United States Patent [19]

Heckele

[11] Patent Number: 5,379,755
[45] Date of Patent: Jan. 10, 1995

[54] DEVICE FOR ATTACHING AND SECURING AN AUXILIARY INSTRUMENT TO A SURGICAL INSTRUMENT

[75] Inventor: Helmut Heckele, Knittlingen, Germany

[73] Assignee: Richard Wolf GmbH, Knittlingen, Germany

[21] Appl. No.: 976,471

[22] Filed: Nov. 16, 1992

[30] Foreign Application Priority Data

Nov. 14, 1991 [DE] Germany .............. 4137426

[51] Int. Cl.$^6$ .............................. A61B 17/32
[52] U.S. Cl. .................................. 128/4; 128/10
[58] Field of Search ............ 128/3, 4, 10, 11, 12, 128/13, 17, 18; 604/165

[56] References Cited

U.S. PATENT DOCUMENTS

| | | |
|---|---|---|
| 373,362 | 11/1887 | Hamilton ............ 128/3 |
| 1,664,660 | 4/1928 | Cameron ............ 128/4 |
| 2,186,187 | 1/1940 | Wolf . | 
| 2,487,502 | 11/1949 | Willinsky ............ 128/4 |
| 3,320,948 | 5/1967 | Martin . |
| 4,607,620 | 8/1986 | Storz ............ 128/4 |
| 4,696,544 | 9/1987 | Costella ............ 128/4 |
| 4,784,463 | 11/1988 | Miyazaki ............ 128/4 |
| 4,846,805 | 7/1989 | Sitar ............ 604/165 |
| 5,205,280 | 4/1993 | Dennison, Jr. et al. ............ 128/4 |

FOREIGN PATENT DOCUMENTS

| | | |
|---|---|---|
| 79373 | 4/1894 | Germany . |
| 606742 | 12/1934 | Germany ............ 128/4 |
| 1977884 | 2/1968 | Germany . |
| 3319049 | 5/1984 | Germany ............ 128/4 |
| 645492 | 11/1950 | United Kingdom . |
| 1150016 | 4/1969 | United Kingdom . |
| 8911305 | 11/1989 | WIPO ............ 128/4 |

Primary Examiner—Ralph A. Lewis
Attorney, Agent, or Firm—Cohen, Pontani, Lieberman, Pavane

[57] ABSTRACT

The device serves to attach and secure an auxiliary instrument to a surgical instrument, through the shaft of which an auxiliary instrument may be introduced. The device has a receiver, which can be releasably fixed to the shaft on the proximal side, for a coupling part of the auxiliary instrument and a clamping element, which can be adjusted relative to the longitudinal axis of the receiver and is brought to rest frictionally against the outer periphery of the wall of the shaft situated between receiver and clamping element during adjustment.

4 Claims, 2 Drawing Sheets

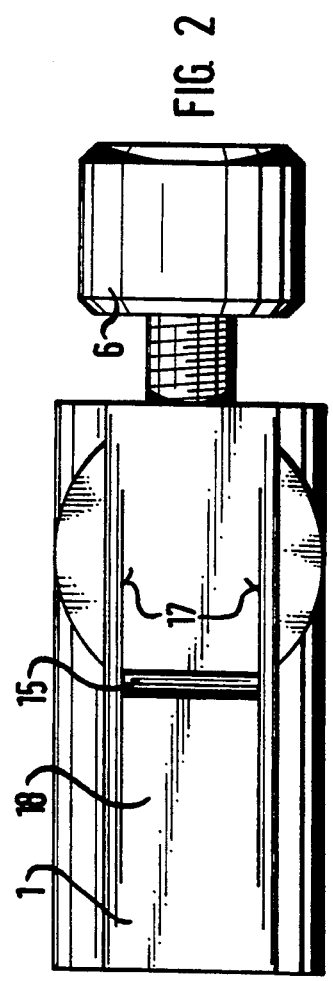
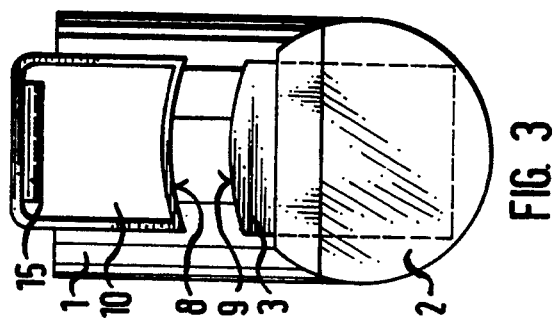
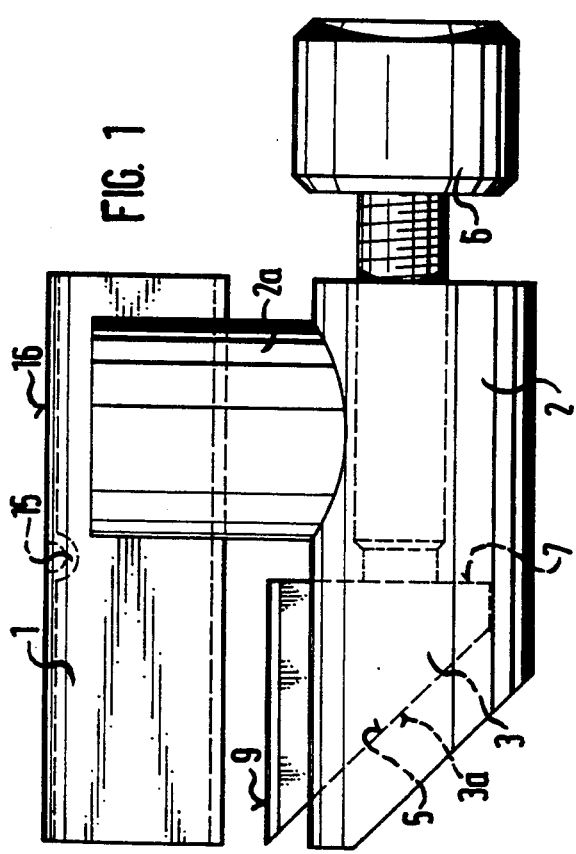

DEVICE FOR ATTACHING AND SECURING AN AUXILIARY INSTRUMENT TO A SURGICAL INSTRUMENT

BACKGROUND OF THE INVENTION a) Field of the Invention

The invention relates to a device for attaching and securing an auxiliary instrument to a surgical instrument, through the shaft of which an auxiliary instrument may be introduced.

When using simple endoscopes, which comprise essentially only one hollow shaft or shaft provided with an introduction channel, it is often necessary to introduce auxiliary instruments and to attach and secure them at the proximal end of the shaft. Auxiliary instruments of this type may be, for example, light-conducting stems, optical systems or operation instruments.

b) Description of the Prior Art

It is known from British patent 1,150,016, for example in the case of bronchoscopes and laryngoscopes, to attach a square stem extending radially outwards onto the proximal end of the shaft, onto which square stem an illuminating device provided with a corresponding square sleeve is pushed and clamped rigidly from the outside, which illuminating device then projects through a peripheral recess in the shaft into the interior thereof. The actual light-conducting stem in this design is inserted into a bore in the square stem extending parallel to the axis of the shaft using an insertion pin.

Furthermore, it is known to make a slot in the proximal end of the shaft in the axial direction and to suspend an angled light-conducting stem in this slot, which light-conducting stem is also secured in turn to an insertion pin in an adaptor bore at the end of the shaft by means of a ball catch element.

The securing of such an insertion pin by means of spring jaws or adjusting screws is also known.

In a further known instrument, a radial bushing or a bushing extending at an angle to the shaft and connected to the interior of the shaft is provided to attach an illuminating device to the proximal end of the shaft, into which bushing the illuminating device can be inserted from the outside and projects into the interior of the shaft using a small prism or mirror.

Since these attachment devices are always only suitable for securing a certain auxiliary instrument in an unalterable position on the shaft, in the case of bronchoscopes, several individual adapter sleeves, or adapter sleeves which can be mounted on the shaft one behind another, are used. Even if the auxiliary instrument can be fixed in the radial direction in this design, a considerable disadvantage does exist in that unintentional release of the mounted adapter sleeves and the instrument parts is possible when manipulating the instrument.

The object of the invention is to provide a device for attaching auxiliary instruments to be introduced into the shaft which is not limited to a certain type and design of these instruments, that is inter alia, can also be used for instrument shafts which are closed at the periphery or those which are divided, and which device can be attached to instrument shafts of different cross-sections in any position. Furthermore, the device should not impede the handling of the instrument.

SUMMARY OF THE INVENTION

In accordance with this object, the invention provides a device for attaching and securing an auxiliary instrument to a surgical instrument, through the shaft of which an auxiliary instrument may be introduced, characterised by a receiver, which can be releasably fixed to the shaft on the proximal side, for a coupling part of the auxiliary instrument and by a clamping element, which can be adjusted relative to the longitudinal axis of the receiver and can be brought to rest frictionally against the outer periphery of the wall of the shaft situated between the receiver and the clamping element during adjustment.

This device gripping the proximal edge of the shaft can be attached to the instrument shafts having different cross-sections, for example even to an expanding laryngoscope. Since it only requires the edge of the shaft for fixed clamping, it may be attached in any radial angular position. Furthermore, the attachment of several attachment devices to the edge of the shaft is possible.

A further advantage of the invention is that the receiver lying in the interior of the shaft can accommodate auxiliary instruments of any construction, for example light-conducting stems may be introduced directly through the receiver, as can further auxiliary instruments of small diameter, whereas other auxiliary instruments can be attached with the aid of a coupling part.

Advantageously, the clamping element is an adjustable wedge, which is suitably adjustable by hand. The wedge may have a clamping surface extending parallel to the longitudinal axis of the receiver and a sliding surface extending at an angle thereto, by means of which it is supported on a correspondingly inclined sliding surface in the device housing, and a working surface extending vertically to the longitudinal axis of the receiver and on which the free end of an adjusting screw arranged eccentrically to the receiver presses or engages.

In order to be able to clamp the shaft of the instrument securely between wedge and receiver, the clamping surface of the clamping element should have a convex shape and the surface of the receiver opposite the clamping element should have a concave shape, wherein the radii of these surfaces are smaller than the radius of the instrument shaft. In order to be able to fix the device securely to the edge of the shaft, the clamping surface of the clamping element may be surface coated or roughened to thus increase the friction.

The passage in the receiver may have any cross-section.

If the auxiliary instrument introduced into the receiver is to be secured against rotation and against axial displacement, the passage in the receiver has a cross-sectional surface deviating from a circular surface, into which a coupling part provided on the auxiliary instrument engages positively and securely against rotation, whereas a protrusion, which can deflect resiliently outwards, also projects into the passage, which protrusion presses on the periphery of the coupling part and fixes the auxiliary instrument frictionally in the receiver.

Suitably, the protrusion consists of a bead on a leaf spring which is formed by two parallel slots in the wall of the receiver.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

FIG. 1 shows a side view of the device to be mounted on an edge of the shaft, FIG. 2 shows a plan view of the device according to FIG. 1, FIG. 3 shows an end view of the device seen from the distal end.

DESCRIPTION OF THE PREFERRED EMBODIMENTS

Figure 4:
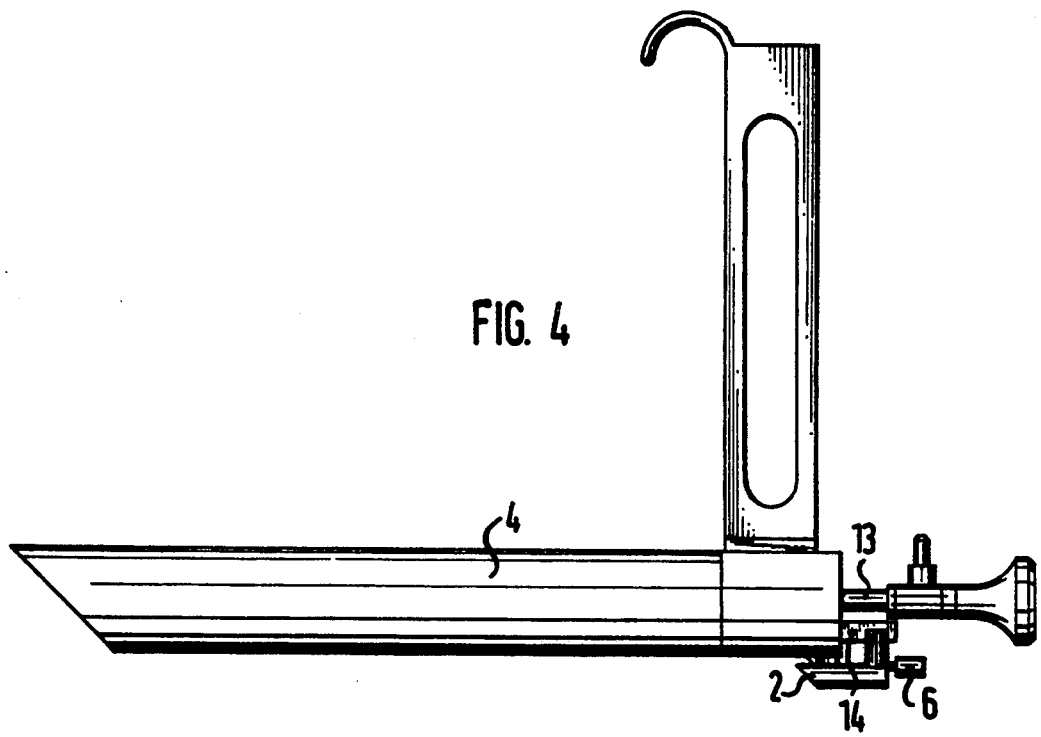
FIG. 4 shows a side view of a laryngoscope with inserted device and an optical system according to FIG. 5 secured by the latter.

The device shown in FIGS. 1 to 3 comprises a receiver 1 and a base 2 with clamping element 3 as parts of the device housing. The receiver 1, which engages in the free lumen of the shaft 4 of an instrument according to FIG. 4, is a sleeve which is described further later on. It is rigidly connected to the base 2 by means of a crosspiece 2a.

The base 2 supports the clamping element 3 at its distal end. The clamping element 3 is a wedge in the exemplary embodiment which sits in a correspondingly shaped recess in the base and according to FIG. 1 rests against a correspondingly inclined sliding surface 5 of the base by means of a sliding surface 3a set at an angle. An adjusting screw 6 is mounted rotatably by hand in a thread in the base. If the screw is rotated in the thread of the base, the wedge 3 is pushed onto the sliding surface 5 relative to the receiver 1, as a result of which the shaft 4 of the instrument is finally fixed between the wedge 3 and the opposing outer periphery of the receiver 1. The free end of the adjusting screw 6 thus engages on the bearing surface 7 of the wedge 3 extending vertically to the longitudinal axis of the receiver 1.

Deviating from the exemplary embodiment, the clamping element may also be a directly acting clamping screw or an eccentric cam instead of the wedge 3. Furthermore, a toggle lever could also be used instead of the wedge and the adjusting screw.

The adjusting screw 6 shown, the base 2 and the clamping element 3 are situated eccentrically to the receiver 1 and hence outside the instrument shaft 4, so that they are not in the way when inserting auxiliary instruments and during other manipulation of the surgical instrument.

The wall of the shaft 4 is clamped between the receiver 1 and the clamping element 3 according to FIG. 4, so that the device grips the proximal end of the shaft 4. It may be attached there at any required position, so that if required several of these devices may optionally also be attached to the proximal end of the instrument shaft 4.

The shaft 4 may have both circular as well as oval, flattened or other cross-section. So that the device acquires a solid seat in any event, a concave shape is provided for the receiver 1 on the side 8 facing the clamping element 3, whereas the clamping element has a convex clamping surface 9. The radii of these surfaces 8, 9 are thus smaller than the radius of the shaft 4 to ensure that three defined mounting lines are produced between the parts 1, 3 and 4 which extend in the axial direction of the shaft 4 and therefore securely centre the device. This effect is also achieved if the clamping surface of the wedge is concave and the opposing surface of the receiver is convex.

Figure 6:
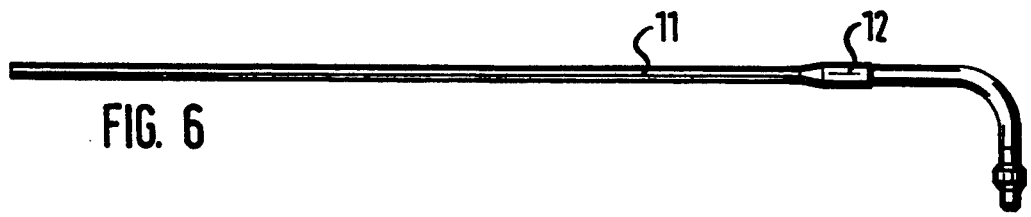
FIG. 6 shows a view of a light-conducting stem.

The passage of the receiver 1 may have a circular cross-section so that auxiliary instruments with a round shaft can be pushed easily into and through the receiver. In this case a region of the auxiliary instrument shaft would form the "coupling part". However, if it is a question of securing the auxiliary instruments against rotation, it is advantagoeus to select a passage 10 deviating from the round cross-section, that is for example an essentially square cross-section, as shown in FIG. 3. Indeed auxiliary instruments having round cross-section can also be pushed into this passage 10, but it is then also possible in accordance with FIG. 6 to provide a light-conducting stem 11 or a further auxiliary instrument at the proximal end with a corresponding square 12 as a coupling part which sits positively and securely against rotation in the passage 10 after introducing the auxiliary instrument into the receiver 1.

Figure 5:
FIG. 5 shows a view of an endoscope optical system with lateral coupling part.

In contrast FIG. 5 shows an optical system 13 representing other auxiliary instruments which has a lateral coupling part 14, the cross-section of which is adapted to that of the passage 10 and which is inserted positively into the receiver 1 after introducing the auxiliary instrument into the shaft 4, whereas the optical system as such extends through the instrument channel outside of the receiver 1.

In addition to securing the auxiliary instrument against rotation as described above, securing the coupling part against slipping axially out of the receiver 1 may also be necessary. For this, the procedure is advantageously carried out such that this securing takes place with the aid of one or more spring elements, and in particular for example by means of a protrusion 15 projecting into the passage 10 in the receiver 1, which protrusion 15 is deflected radially and resiliently outwards when inserting the coupling part 12 or 14 into the receiver 1 and presses against the periphery of the coupling part to connect the latter frictionally with the receiver. There is also the possibility that the protrusion 15 engages in a groove situated in the coupling part 14, as a result of which axial slipping of the coupling part 14 out of the receiver 1 is effectively prevented.

The spring action mentioned may be achieved in that the upper wall 16 of the receiver 1 is provided with two longitudinal slots 17, so that the part situated between the slots forms a leaf spring 18. The protrusion 15 may be formed by means of a bead in this leaf spring, which incidentally may also have a multi-part design and may have more than one bead.

The present invention may be embodied in other specific forms without departing from the spirit or essential attributes thereof and, accordingly, reference should be made to the appended claims rather than to the foregoing specification as indicating the scope of the invention.

I claim:

1. A device for attaching and securing an auxiliary instrument having a coupling part to a surgical instrument having a walled shaft through which the auxiliary instrument may be introduced, comprising: a receiver having a longitudinal axis and a passage along the longitudinal axis, in which passage the coupling part of the auxiliary instrument is insertable; a base member connected to the receiver and having an inclined sliding surface; and clamping means for releasably clamping the receiver to the shaft of the surgical instrument, said clamping means including a wedge-shaped clamping element which is movable and slidable relative to the longitudinal axis of the receiver so that the clamping element is able to frictionally rest against the outer periphery of the shaft wall, the wedge-shaped element having a clamping surface extending parallel to the longitudinal axis of the receiver and a sliding surface extending at an angle thereto so as to correspond to the inclined sliding surface of the base member, the inclined sliding surface of the wedge-shaped element being supported on the correspondingly inclined sliding surface in the base member, the wedge-shaped element further having a working surface extending vertically to the longitudinal axis of the receiver, the clamping means further including an adjusting screw rotatably mounted in the base member so as to be arranged eccentrically to the receiver and having a free end which engages the working surface of the wedge-shaped element.

2. Device according to claim 1, wherein the instrument shaft has a radius, the clamping element having a clamping surface with a convex shape and the receiver having a concave-shaped surface arranged opposite the clamping surface of the clamping element, the concave and convex surfaces having radii that are smaller than the radius of the instrument shaft.

3. Device according to claim 1, and further comprising at least one protrusion provided so as to project inwardly from a wall of the receiver into the receiver passage and so as to be outwardly deflectable from the coupling part of the auxiliary instrument against spring action.

4. Device according to claim 3, wherein the protrusion is a bead on a leaf spring which is formed by two parallel slots in the wall of the receiver.

* * * * *